United States Patent

Schwalm et al.

(10) Patent No.: US 6,960,637 B2
(45) Date of Patent: Nov. 1, 2005

(54) POLYMERS BASED ON FLUORANTHENE AND THEIR USE

(75) Inventors: Reinhold Schwalm, Wachenheim (DE); Yvonne Heischkel, Mannheim (DE); Horst Weiss, Neuhofen (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/377,788

(22) Filed: Mar. 4, 2003

(65) Prior Publication Data

US 2003/0181617 A1 Sep. 25, 2003

(30) Foreign Application Priority Data

Mar. 15, 2002 (DE) ......................... 102 11 648

(51) Int. Cl.⁷ .............................................. C08F 10/14
(52) U.S. Cl. ......................... 526/280; 526/346; 526/348
(58) Field of Search ............................. 526/280, 346, 526/348

(56) References Cited

U.S. PATENT DOCUMENTS

| 5,281,489 A | 1/1994 | Mori et al. |
| 5,777,070 A | 7/1998 | Inbasekaran et al. |
| 6,127,516 A | 10/2000 | Bard et al. |
| 2001/0026878 A1 | 10/2001 | Woo et al. |

FOREIGN PATENT DOCUMENTS

| DE | 44 14 693 | 11/1995 | |
| DE | 4414693 A1 * | 11/1995 | ............. C09B/1/48 |
| EP | 0 329 322 | 8/1989 | |
| RU | 412 205 | 9/1974 | |
| WO | WO 00/46321 | 8/2000 | |

OTHER PUBLICATIONS

Mark T. Bernius, et al. "Progress with Light–Emitting Polymers," Advanced Materials, vol. 12, No. 23, Dec. 1, 2000, pp. 1737–1750.

R.J. Waltman, et al. "Electrically Conducting Polymers: A Review of the Electropolymerization Reaction, of the Effects of Chemical Structure on Polymer Film Properties, and of Applications Towards Technology," Can. J. Chem., vol. 64, 1986, pp. 76–95.

* cited by examiner

Primary Examiner—William K. Cheung
(74) Attorney, Agent, or Firm—Oblon, Spivak, McClelland, Maier & Neustadt, P.C.

(57) ABSTRACT

Polymers comprising repeating units of the formula I:

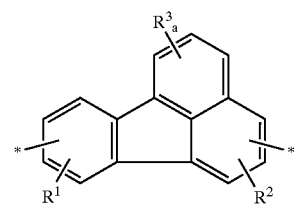

where the variables are defined as follows:

a is an integer from 0 to 3, $R^1$, $R^2$, $R^3$ are identical or different and are selected independently from among hydrogen, $C_1$–$C_{20}$-alkyl, $C_1$–$C_{20}$-alkyl containing one or more Si, N, P, O or S atoms, $C_6$–$C_{30}$-aryl, preferably $C_6$–$C_{14}$-aryl, $C_4$–$C_{14}$-heteroaryl, —N($C_6$–$C_{14}$-aryl)$_2$, and $Y^1$, where $Y^1$ may be identical or different and are selected from among —CH=CH$_2$, trans- or cis-CH=CH—$C_6H_5$, acryloyl, methacryloyl, methylstyryl, O—CH=CH$_2$ and glycidyl,

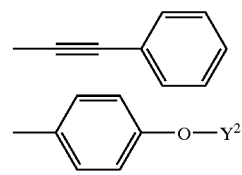

where $Y^2$ is selected from among —CH=CH$_2$, trans- or cis-CH=CH—$C_6H_5$, acryloyl, methacryloyl, methylstyryl, —O—CH=CH$_2$ and glycidyl, and one or more groups $Y^1$ or $Y^2$ may be crosslinked to one another.

14 Claims, No Drawings

POLYMERS BASED ON FLUORANTHENE AND THEIR USE

The present invention relates to polymers comprising repeating units of the formula I

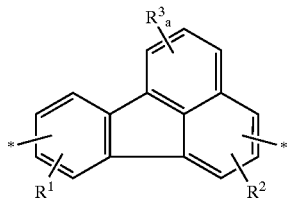

where the variables are defined as follows:
a is an integer from 0 to 33,
$R^1$, $R^2$, $R^3$ are identical or different and are selected independently from among hydrogen, $C_1$–$C_{20}$-alkyl, $C_1$–$C_{20}$-alkyl containing one or more Si, N, P, O or S atoms, $C_6$–$C_{30}$-aryl, preferably $C_6$–$C_{14}$-aryl, $C_4$–$C_{14}$-heteroaryl containing at least one S or N atom, —N($C_6$–$C_{14}$-aryl)$_2$, and $Y^1$, where $Y^1$ may be identical or different and are selected from among —CH=CH$_2$, trans- or cis-CH=CH—C$_6$H$_5$, acryloyl, methacryloyl, methylstyryl, O—CH=CH$_2$ and glycidyl,

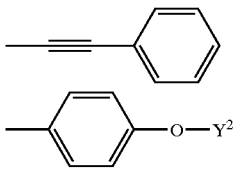

where $Y^2$ is selected from among —CH=CH$_2$, trans- or cis-CH=CH—C$_6$H$_5$, acryloyl, methacryloyl, methylstyryl, —O—CH=CH$_2$ and glycidyl, and one or more groups $Y^1$ or $Y^2$ may be crosslinked to one another.

Electrically conductive polymers are of increasing economic and industrial importance, for example in the field of electroluminescent diodes. These can be used in a variety of ways, for example as displays in mobile telephones or for visual display units in the computer sector.

Organic electroluminescent diodes usually comprise a cathode and an anode which are separated by at least one film, more preferably at least two films, of an organic material. The films typically have a thickness which does not exceed 0.2 μm. The two electrodes are advantageously made of different materials whose conduction band or valence band are close to the potentials of the HOMO and LUMO energy levels of the polymers concerned. At least one of the electrodes, either cathode or anode, comprises a metal film or a metal oxide film which has a thickness of about 0.2 μm and is optically transparent.

A review of organic electroluminescent diodes has been published by, for example M. T. Bernius et al. in Adv. Mat. 2000, 12, 1737. The polymers have to meet demanding requirements and known materials are usually not able to meet all the demands made of them. It has been found that it is not only the choice of monomers which is of great importance for the usability of the polymers.

Polymers based on fluoranthene and possibly other (co)monomers are known per se. They are usually prepared by electrochemical coupling reactions, cf., for example, R. J. Waltman et al., J. Electrochem. Sci. 1985, 132, 631. The formation of structurally very nonuniform polymers having a high polydispersity and low glass transition temperatures is observed.

U.S. Pat. No. 5,281,489 discloses the use of monomeric fluoranthene in organic electroluminescent diodes. However, monomeric fluoranthene can migrate under the conditions of use. The layer of monomeric fluoranthene is not stable, which results in a short life of the diodes.

U.S. Pat. No. 6,127,516 discloses electrochromic materials based on 7,10-diphenylacenaphthofluoranthene, which can be produced by deposition on electrode surfaces. The molecular weight distribution is usually too broad for use in diodes.

U.S. Pat. No. 5,777,070 discloses a process for preparing conjugated polymers which is based on the Suzuki coupling of monomers containing internal groups, for example of the ethylene, acetylene, phenylene, fluorene, fluoranthene, anthracene, phenanthrene, etc., type and is carried out in the presence of a phase transfer catalyst. The Suzuki coupling of monomers based on fluorene is described by way of example. However, the life of electroluminescent diodes comprising polyfluorenes is still in need of improvement.

WO 00/46321 discloses electrically conductive fluorene copolymers comprising at least 10 mol % of 9-monosubstituted and/or 9,9-disubstituted fluorene units.

It is an object of the present invention to provide novel electrically conductive polymers which are suitable for use in diodes. A further object is to provide a process for preparing the polymers of the present invention. Finally, it is also an object of the invention to provide new uses and application methods for the polymers of the present invention.

We have found that the first of these objects is achieved by the polymers defined at the outset.

For the purposes of the present invention, the nomenclature of fluoranthenes is according to the scheme below:

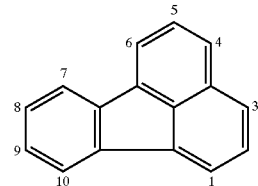

In the formula I, the variables are defined as follows.
a is an integer from 0 to 3, preferably 0 or 1 and very particularly preferably 0.
$R^1$, $R^2$, $R^3$ are identical or different and are selected independently from among hydrogen, $C_1$–$C_{20}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl n-octyl, n-decyl, n-dodecyl and n-octadecyl; preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;
$C_1$–$C_{20}$-alkyl containing one or more Si, N, P, O— or S-atoms, for example —CH$_2$—CH$_2$—OCH$_3$, —[CH$_2$—CH$_2$]$_2$—OCH$_3$, —[CH$_2$—CH$_2$]$_3$—OCH$_3$, —[CH$_2$—CH$_2$]$_3$—OC$_2$H$_5$, —[CH$_2$—CH$_2$]$_3$—O-n-C$_3$H$_7$, —[CH$_2$—CH$_2$]$_3$—O—i—C$_3$H$_7$, —[CH$_2$—CH$_2$]$_3$-n-OC$_4$H$_9$,
—CH$_2$—CH$_2$—SCH$_3$, —CH$_2$—CH$_2$—N(CH$_3$)$_2$, —CH$_2$—CH—(OCH$_3$)$_2$, —CH$_2$—CH$_2$—P(CH$_3$)$_2$, —CH$_2$—CH$_2$—Si(CH$_3$)$_3$, —CH$_2$—CH$_2$—OSi(CH$_3$)$_3$;

$C_6$–$C_{30}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, 9-fluorenyl or 2,8-indenofluorenyl, preferably $C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, 9-fluorenyl, particularly preferably phenyl, 1-naphthyl and 2-naphthyl, particularly preferably phenyl;

$C_4$–$C_{14}$-heteroaryl containing one or more S- or N-atoms, for example N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl;

—N($C_6$–$C_{14}$-aryl)$_2$, where $C_6$–$C_{14}$-aryl may be identical or different and are as defined above;

one or more groups $Y^1$, where $Y^1$ may be identical or different and are selected from among —CH=CH$_2$, trans- or cis-CH=CH—$C_6H_5$, acryloyl, methacryloyl, α-methylstyryl or para-methylstyryl, —O—CH=CH$_2$ and glycidyl,

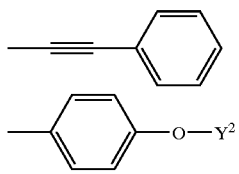

where $Y^2$ is selected from among acryloyl, methacryloyl, α-methylstyryl or para-methylstyryl, O—CH=CH$_2$ and glycidyl, and one or more groups $Y^1$ or $Y^2$ may be crosslinked to one another.

Preference is given to polymers comprising repeating units of the formula Ia:

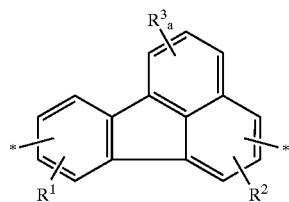

Ia where a is 0 or 1 and the other variables are as defined above. Very particular preference is given to a being 0 and $R^1$ and $R^2$ each being hydrogen.

For the purposes of the present invention, the term polymers also encompasses compounds which have only 2 repeating units of the formula I or Ia and have a radical capping each end. Furthermore, the term "polymers" used in the context of the present invention also encompasses compounds which are made up of one repeating unit of the formula I or Ia and at least one comonomer unit which forms a conjugated system with the repeating unit I or Ia. Examples are para-phenylene units, trans- or cis-ethylene units, acetylene units, 1,4-naphthylene units, 1,5-naphthylene units, 1,4-anthrylene units, 9,10-anthrylene units, also $C_4$–$C_{14}$-heteroarylene units containing N, S and/or O as heteroatoms, for example 2,5-thiophene units, with the thiophene units preferably being substituted in the 3 and 4 positions, 2,7-carbazolylene units, 2,5-pyridylene units, where the comonomer units may also bear additional substituents, for example cyano, $C_1$–$C_6$-alkoxy of di-$C_1$–$C_6$-alkylamino substituents. Further suitable comonomer units are:

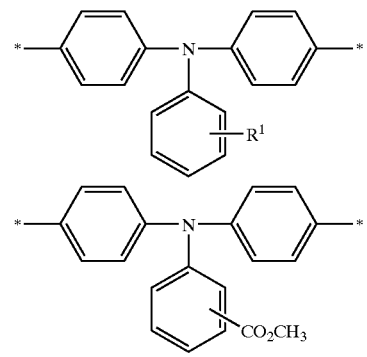

The polymers of the present invention comprise from 1 to 10 repeating units of the formula I or Ia, preferably from 2 to 4, particularly preferably from 2 to 3, repeating units of the formula I or Ia. If the polymers of the present invention have only 1 repeating unit of the formula I or Ia, they have from 1 to 300 comonomer units, and if they have at least two repeating units of the formula I or Ia, they have from 0 to 300, preferably up to 50, in particular up to 10, co-repeating units.

The polydispersity $M_w/M_n$ of the polymers of the present invention is preferably from 1.1 to 3.5.

The polymers are usually capped at the ends by a radical selected from among hydrogen, $C_6$–$C_{14}$-aryl and $C_4$–$C_{14}$-heteroaryl, with the radicals being as defined above.

A further aspect of the present invention is a process for preparing the polymers of the present invention. The polymers of the present invention are preferably prepared by reactions of organometallic chemistry, for example by Yamada coupling or by means of a Suzuki reaction. Preference is given to a process starting out from monomers of the formula II:

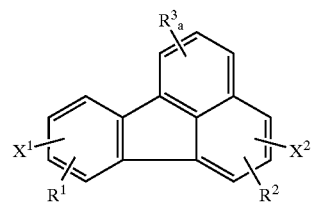

II and in particular of the formula IIa,

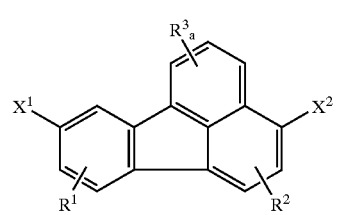

IIa where the variables are defined as follows:
$X^1$ and $X^2$ are identical or different and are selected from among halogen, for example chlorine, bromine or iodine, in particular chlorine or bromine, and esterified sulfonate such as para-toluenesulfonate (tosylate), triflate (CF$_3$—SO$_3$—), para-nitrophenylsulfonate ("nosylate"), para-bromosulfonate ("brosylate"), in particular triflate; boron-containing radicals of the formula —B(O—[C(R$^6$)$_2$]$_n$)—O), where R$^6$ are identical or different and are selected from among hydrogen and C$_1$–C$_{20}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl n-octyl, n-decyl, n-dodecyl and n-octadecyl; preferably C$_1$–C$_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably C$_1$–C$_4$-alkyl such as methyl, ethyl, n-propyl, isopropyl, n-butyl, isobutyl, sec-butyl and tert-butyl, very particularly preferably methyl;

n is an integer from 2 to 10, preferably from 2 to 5.

Very particular preference is given to boron-containing radicals of the formula:

—B(O—[C(CH$_3$)$_2$]$_2$)—O).

Two alternative ways of carrying out the process of the present invention are, firstly, to use a monomer of the formula II in which X$^1$ is selected from among halogen and esterified sulfonate and X$^2$ is selected from among boron-containing radicals and, secondly, to use at least two different monomers of the formula II of which one monomer has two halogen atoms or two esterified sulfonate groups or one halogen atom and one esterified sulfonate group and the other monomer has two boron-containing radicals —B(O—[C(R$^6$)$_2$]$_n$)—O). In the latter case, it needs to be ensured that the molar ratio of the sum of halogen and esterified sulfonate to boron-containing radicals is from 0.8:1 to 1.2:1.

The polymerization is preferably carried out in the presence of a nickel or palladium compound in which the metal is particularly preferably in the oxidation state 0. Very particular preference is given to the commercially available tetrakis(triphenylphosphine)palladium [Pd{P(C$_6$H$_5$)$_3$}$_4$] and also commercially available nickel compounds, for example Ni(C$_2$H$_4$)$_3$, Ni(1,5-cyclooctadiene)$_2$ "Ni(COD)$_2$", Ni(1,6-cyclodecadiene)$_2$, or Ni(1,5,9-all-trans-cyclododecatriene)$_2$. Particular preference is given to Ni[COD]$_2$. To carry out the polymerization, an excess of P(C$_6$H$_5$)$_3$ or 1,5-cyclooctadiene can be added. When the polymerization is carried out in the presence of palladium compounds, it is usually sufficient to use catalytic amounts, i.e. from 0.1 to 10 mol % of Pd, based on monomer of the formula II or IIa. If the polymerization is to be carried out in the presence of nickel compounds, stochiometric amounts of Ni, based on the sum of monomers of the formula II or IIa and any comonomer, are usually required.

The polymerization is usually carried out in an organic solvent, for example toluene, ethylbenzene, meta-xylene, ortho-xylene, dimethylformamide DMF, tetrahydrofuran, dioxane or mixtures of these. The solvent or solvents is/are freed of traces of moisture by methods customary in the laboratory prior to the polymerization. The polymerization is usually carried out under protective gas; suitable protective gases are nitrogen and noble gases, in particular argon, and CO$_2$.

The polymerization is usually carried out in the presence of a base, for example an organic amine. Triethylamine, pyridine and collidine are particularly useful.

The polymerization can also be carried out in the presence of solid basic salts, for example alkali metal carbonate or alkali metal bicarbonate, in the presence or absence of a crown ether such as 18-crown 6. It is also possible to carry out the polymerization as a two-phase reaction using aqueous solutions of alkali metal carbonate, in the presence or absence of a phase transfer catalyst. In this case, it is not necessary to free the organic solvent of moisture prior to the reaction.

The polymerization usually takes from 10 minutes to 2 days, preferably from 2 hours to 24 hours. The pressure conditions are not critical, and preference is given to atmospheric pressure. The polymerization is usually carried out at elevated temperature, generally from 80° C. to the boiling point of the organic solvent or solvent mixture, in particular from 100° C. to the boiling point of the organic solvent or solvent mixture.

If copolymers of monomers of the formula IIand the above-described comonomers are to be prepared, the comonomers used are the appropriate para-phenylene compounds, trans- or cis-ethylene compounds, acetylene compounds, 1,4-naphthylene compounds, 1,5-naphthylene compounds, 1,4-anthrylene compounds, 9,10-anthrylene compounds and/or 2,5-thiophene compounds which bear the abovementioned radicals X$^1$ and X$^2$, with the abovementioned proviso regarding the molar ratios of halogen and esterified sulfonate to boron-containing radicals.

A further aspect of the present invention is monomers of the formula III,

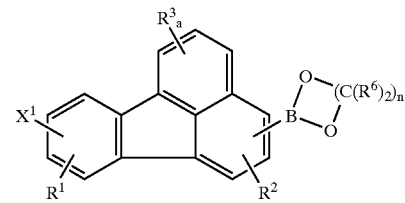

III in particular of the formula IIIa,

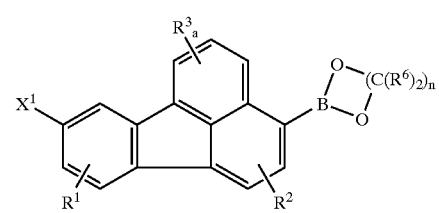

III a where the variables are as defined above. Monomers of the formula III and in particular of the formula IIIa are used for preparing the polymers of the present invention. A further aspect of the present invention is a process for preparing the novel monomers of the formula III and in particular IIIa. The process of the present invention starts out from compounds of the formula IV or IVa,

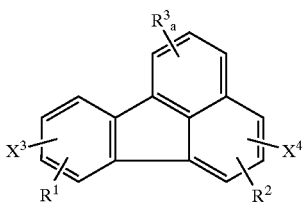

IV

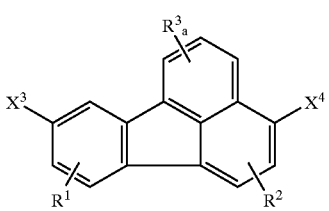

IVa where $X^3$ and $X^4$ are each halogen, in particular chlorine or bromine, or esterified sulfonate, in particular triflate ($CF_3$—$SO_3$—).

To carry out the process of the present invention, the compounds of the formula IV and in particular of the formula IV a are firstly singly or doubly metalated by means of at least two or at least four equivalents of a strong organometallic base and the products are subsequently reacted with one or two equivalents of a boron compound of the formula V:

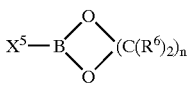

V where the variables $R^6$ and n are as defined above and $X^5$ is selected from among $C_1$–$C_6$-alkoxy such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy, isopropoxy and n-butoxy. $X^5$ is very particularly preferably isopropoxy.

Bases which can be used are the metal alkyls customary in organometallic chemistry, for example methyllithium, ethyllithium, n-butyllithium, sec-butyllithium, tert-butyllithium or hexyllithium, also Grignard compounds such as ethylmagnesium bromide. Solvents which have been found to be useful are high-boiling solvents such as toluene, ortho-xylene, meta-xylene, para-xylene, ethylbenzene or mixtures of these, also noncyclic or cyclic ethers such as 1,2-dimethoxyethane, tetrahydrofuran, dioxane or diethyl ether.

The metalation is generally complete after a few hours; a reaction time of from 1 to 10 hours is appropriate and preference is given to from 2 to 5 hours. The temperature conditions are generally not critical, and carrying out the reaction at from −90° C. to −20° C. has been found to be preferred.

The singly or doubly metalated compound of the formula IV or IV a is subsequently reacted with at least one or two equivalents of a boron compound of the formula V. For this purpose, the two components are mixed with one another in a suitable solvent such as benzene, toluene, ethylbenzene, orthoxylene, meta-xylene or para-xylene, chlorobenzene, cyclohexane, acetonitrile, tetrahydrofuran, 1,2-dimethoxyethane, dioxane or diethyl ether or a mixture thereof. The reaction can be carried out at from −100° C. to +150° C., preferably from −78° C. to +100° C. It is important that the reaction is carried out in the absence of oxygen and moisture.

The pressure conditions are generally not critical, and preference is given to atmospheric pressure. The preferred reaction time is from 10 minutes to 2 days, more preferably from 1 hour to 24 hours.

The work-up and purification of the novel monomers of the formula III or IIIa can be carried out by conventional methods, for example extraction, permeation, crystallization, chromatography, precipitation or sublimation.

Boron compounds of the formula V can be synthesized readily, and some derivatives are commercially available from Sigma-Aldrich.

The compounds of the formula IV or IV a can be obtained from fluoranthene or the appropriate fluoranthene derivatives by reactions or reaction sequences which are known in principle. The preparation of the very particularly preferred compounds IVa.1 and IVa.2:

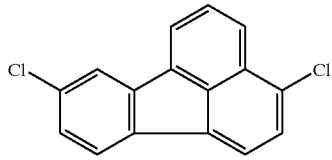

IV a.1

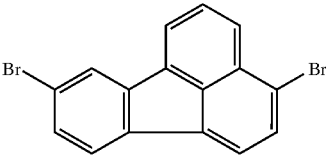

IV a.2 is carried out, for example, by chlorination or bromination of unsubstituted fluoranthene in, for example, glacial acetic acid or nitrobenzene using two equivalents of $Cl_2$ or $Br_2$. The preparation of the very particularly preferred compounds IV a.3 and IV a.4

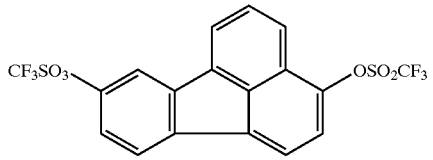

IV a.3

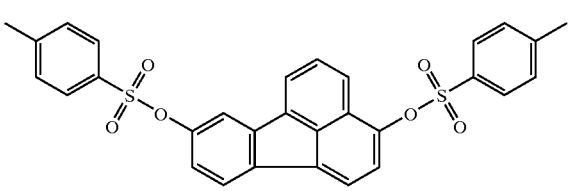

IV a.4 can be carried out, for example, by dinitration of fluoranthene, subsequent reduction of the nitro groups to amino groups, diazotization of the amino groups using $NaNO_2$/HCl or amyl nitrite and thermal decomposition of the diazonium salts and subsequent reaction of the phenolic OH groups with $CF_3SO_2Cl$ to form the bis-triflate IV a.3 or with para-$CH_3$—$C_6H_4$—$SO_2Cl$ to form the bis-tosylate IV a.4.

A further aspect of the present invention is a further process for preparing the polymers of the present invention.

In this process, preference is given to photochemically or thermally polymerizing monomers of the formula VI:

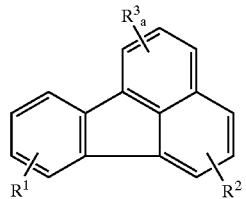
VI where at least one, preferably two, of the radicals $R^1$ to $R^3$ is/are selected from $Y^1$, where $Y^1$ are identical or different and are selected from among —CH=CH$_2$, trans- or cis-CH=CH—C$_6$H$_5$, acryloyl, methacryloyl, α-methylstyryl and para-methylstyryl, —O—CH=CH$_2$ and glycidyl,

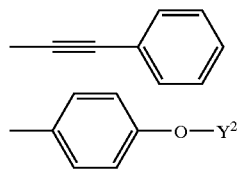

where $Y^2$ is selected from among acryloyl, methacryloyl, α-methylstyryl and para-methylstyryl, —O—CH=CH$_2$ and glycidyl, and the other radicals are as defined above, with one another.

Preference is given to thermally or photochemically polymerizing or copolymerizing monomers of the formula VIa:

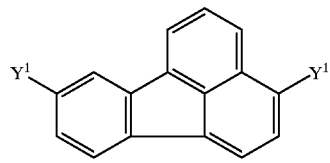
VIa with one another.

A thermal polymerization or copolymerization is preferably carried out by applying monomers of the formula VI or VIa in which at least one, preferably two, of the radicals $R^1$ to $R^3$ are selected from among readily thermally polymerizable radicals $Y^1$ which may be identical or different and are selected from among trans- or cis-CH=CH—C$_6$H$_5$, α-methylstyryl and para-methylstyryl,

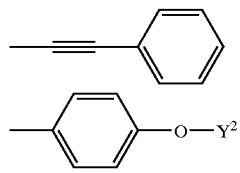

where $Y^2$ is trans- or cis-CH=CH—C$_6$H$_5$, α-methylstyryl or para-methylstyryl, as such or as a solution, if appropriate together with comonomers, as a film, preferably on one of the electrodes, and heating this film for from 10 minutes to 1 hour under nitrogen or noble gas. A temperature range from 40 to 120° C. has been found to be useful. Any comonomers present likewise have to bear at least one, preferably two, of the above-described readily thermally polymerizable radicals $Y^1$ per molecule.

A photochemical polymerization or copolymerization is preferably carried out by applying monomers of the formula VI or VIa in which at least one, preferably two, of the radicals $R^1$ to $R^3$ is/are selected from among readily photochemically polymerizable radicals $Y^1$ which may be identical or different and are selected from among acryloyl, methacryloyl, —O—CH=CH$_2$ and glycidyl and

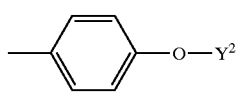

where $Y^2$ is selected from among acryloyl, methacryloyl, —O—CH=CH$_2$ and glycidyl, as such or as a solution, if appropriate together with comonomers, as a film preferably on one of the electrodes, and illuminating this film with a radiation source, for example a UV lamp, in the presence of a customary photoinitiator known from the photopolymerization of, for example, acrylic acid derivatives or methacrylic acid derivatives or unsaturated ethers. Any comonomers present likewise have to bear at least one, preferably two, of the above-described readily photochemically polymerizable radicals $Y^1$ per molecule.

The monomers of the formula VI or VIa can be prepared from, for example, compounds of the formula IV, in particular IV a.1 to IV a.4, by reactions known in principle, for example the Hecke reaction or the Stille coupling.

The polymers of the present invention can comprise units of the formula VII, preferably VIIa,

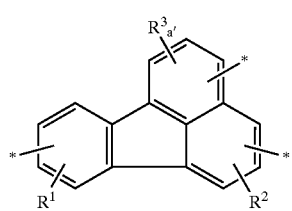
VII

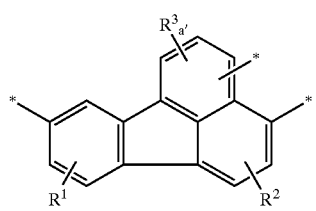
VII a where a' is an integer from 0 to 2, preferably from 0 to 1 and particularly preferably 0, and the other variables are as defined above. Polymers comprising monomer units of the formula VII or VIIa can be synthesized by addition of, for example, monomers of the formula VIIIa–d:

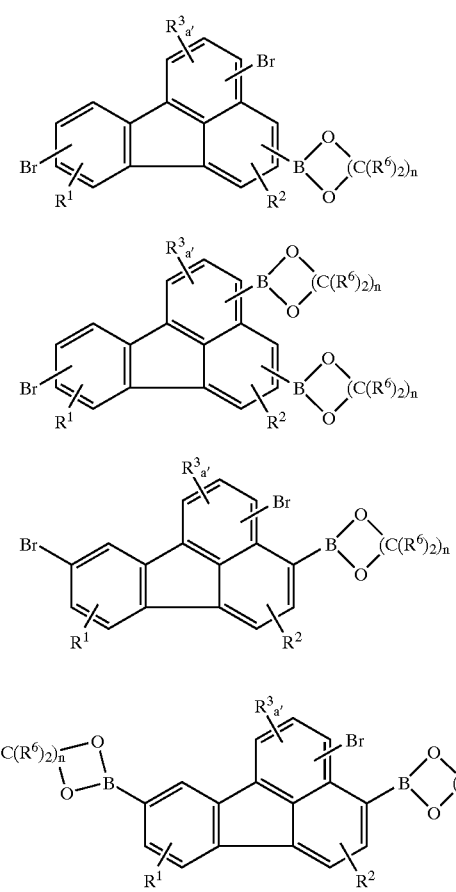

VIII a

VIII b

VIIIc

VIII d during the palladium- or nickel-catalyzed polymerization of the monomers of the formula II or IIa.

Further aspects of the present invention are the use of the novel polymers comprising repeating units of the formula I or Ia for producing organic electroluminescent diodes and also organic electroluminescent diodes produced using the polymers of the present invention. The organic electroluminescent diodes of the present invention comprise at least one organic film, advantageously at least two organic films, of which at least one has electroluminescent properties and comprises an electroluminescent polymer according to the present invention. The organic electroluminescent diodes of the present invention further comprise a cathode and an anode which are separated by at least one film, more preferably at least two films. The films advantageously have a thickness which does not exceed 0.1 µm. The two electrodes are advantageously made up of different materials whose conduction band or valence band is close to the potentials of the HOMO and LUMO energy levels of the polymers of the present invention. At least one of the electrodes, either cathode or anode, comprises a metal film or a metal oxide film which has a thickness of about 0.2 µm. The electroluminescent diodes of the present invention can be produced, for example, by applying a film comprising or consisting of the polymers of the present invention having a thickness of from 0.02 to 0.2 µm between a cathode and an anode. Another method is to apply one or more films of which at least one consists of a polymer comprising one or more polymers according to the present invention to an electrode and subsequently to attach the second electrode. One of the electrodes is optically transparent.

If an electric field or an electric potential is then applied, electrons are injected into the lowest unoccupied energy level (LUMO) or holes are injected into the highest occupied energy level (HOMO) of the polymer of the present invention and light emission occurs by recombination of the charge carriers.

The application of the polymers of the present invention is usually carried out from a solution in an organic solvent such as an ether, a chlorinated hydrocarbon such as methylene chloride or an aromatic hydrocarbon such as toluene. The application itself can be carried out by conventional techniques, for example film-forming coating (screen printing technique), by application using an ink jet printer, by stamp printing, for example by PDMS, namely stamp printing by means of a silicone rubber stamp which has been photochemically structured.

The electroluminescent films of the present invention which comprise polymers of the present invention or consist of these usually have a thickness of from 0.01 to 0.4 µm, preferably from 0.05 to 0.2 µm. They can further comprise other constituents which are generally customary in production of organic electroluminescent diodes. The films of the present invention can be used for producing organic electroluminescent diodes; compared to electroluminescent diodes known from the prior art, these have a longer life and further advantageous properties.

The invention is illustrated by the examples.

Synthesis of Compound IIIa.1

III a.1

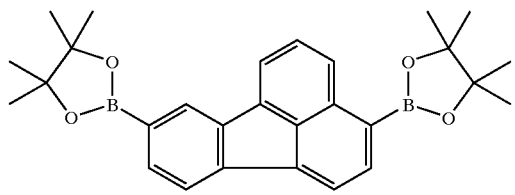

8 g of 3,8-dibromofluoranthene IV a.2, prepared by dibromination of fluoranthene in nitrobenzene, were dissolved in 90 ml of THF under protective gas and cooled to −5° C. 61 ml of tert-butyllithium solution (15% strength by weight in pentane) were added dropwise and the mixture was stirred at room temperature for 1.5 hours. 9.5 ml of 2-isopropoxy-4,4,5,5-tetramethyl-1,3,2-dioxaborolane were added dropwise at such a rate that the temperature did not exceed 5–20° C. The reaction mixture was stirred at room temperature for a further 15 hours. The reaction mixture was poured into water and extracted a number of times (at least 3 times) with diethyl ether, the ether phase was dried over $MgSO_4$, concentrated by evaporation and purified by chromatography on silica gel (Merck silica gel 60). Nonpolar impurities were eluted with cyclohexane, and the product was subsequently eluted with ethyl acetate/cyclohexane (volume ratio=1:9). Yield: 50% as a yellow solid. The structure was confirmed by $^1$H-NMR spectroscopy.

POLYMERIZATION EXAMPLE 1.56 mmol of 3,8-dibromofluoranthene IV a.2, 1.58 mmol of dipinacolyl fluoranthene-3,8-diboronate (Compound IIIa.1), 0.011 mmol of phase transfer catalyst Aliquat® 336, commercially available from Aldrich, and 2.5 ml of 2 molar aqueous sodium carbonate solution were mixed with 14 ml of toluene and degassed by means of nitrogen. 1.33 ml of a 0.1% strength by weight solution of tetrakis(triphenylphosphine)palladium in toluene were added. The mixture was maintained at 90–100° C. for 48 hours under argon. Finally, 0.82 ml of a 1% strength by weight solution of bromobenzene in toluene was added and the mixture was stirred at the same temperature for a further 24 hours.

For the work-up, the reaction solution was added dropwise to 50 ml of a dilute methanolic HCl solution. The solid which precipitated was filtered off, purified over silica gel (Merck silica gel 60, eluant: toluene) and precipitated in methanol. The precipitation/silica gel purification procedure was repeated another three times. The product was obtained as a yellowish powder.

We claim:

1. A polymer, comprising:
repeating units of the formula I:

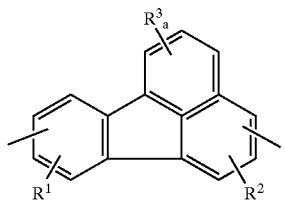

I wherein the variables are defined as follows:
a is an integer from 0 to 3,
$R^1$, $R^2$, $R^3$ are identical or different and are selected independently from the group consisting of hydrogen, $C_1$–$C_{20}$-alkyl, $C_1$–$C_{20}$-alkyl containing one or more Si, N, P, O or S atoms, $C_6$–$C_{30}$-aryl, $C_4$–$C_{14}$-heteroaryl containing at least one S or N atom, —N($C_6$–$C_{14}$-aryl)$_2$, and $Y^1$,
wherein $Y^1$ may be identical or different and is selected from the group consisting of —CH=CH$_2$, trans-CH=CH—C$_6$H$_5$, cis—CH=CH—C$_6$H$_5$, acryloyl, methacryloyl, methylstyryl, —O—CH=CH$_2$, glycidyl,

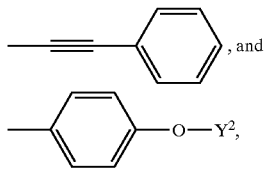

, and wherein $Y^2$ is selected from the group consisting of —CH=CH$_2$, trans-CH=CH—C$_6$H$_5$, cis-CH=CH—C$_6$H$_5$, acryloyl, methacryloyl, methylstyryl, —O—CH=CH$_2$, glycidyl, and one or more groups $Y^1$ or $Y^2$ may be crosslinked to one another.

2. The polymer as claimed in claim 1, comprising; repeating units of the formula Ia:

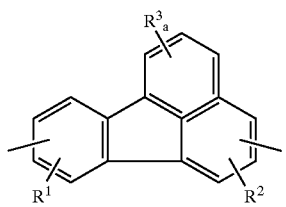

Ia wherein a is 0 or 1 and the other variables are as defined above.

3. The polymer as claimed in claim 1, comprising: from 1 to 10 repeating units of the formula I.

4. The polymer as claimed in claim 1 or 2, wherein a is 0.

5. The polymer as claimed in claim 1, comprising from 2 to 4 repeating units of the formula I.

6. A process for preparing a polymer as claimed in claim 1 or 2, which comprises:
reacting one or more monomers of the formula II:

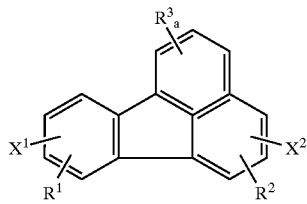

II with one another in the presence of a nickel or palladium compound, wherein the variables $R^1$ to $R^3$ and a are as defined above,
$X^1$ and $X^2$ are identical or different and are selected from the group consisting of halogen, esterified sulfonate and boron-containing radicals of the formula —B(O—[C(R$^6$)$_2$]$_n$)—O), wherein $R^6$ are identical or different and are each, depending on one another, hydrogen or $C_1$–$C_{20}$-alkyl, and n is an integer from 2 to 10;
with the proviso that
a) either a monomer of the formula II in which
$X^1$ is selected from the group consisting of halogen and esterified sulfonate, and
$X^2$ is at least one boron-containing radical,
is used, or
b) at least two different monomers of the formula II of which
one monomer has i) two halogen, ii) two esterified sulfonate groups or iii) one halogen and one esterified sulfonate group, and
the other monomer has two boron-containing radicals —B(O—[C(R$^6$)$_2$]$_n$—O), are used, and
wherein the molar ratio of the sum of halogen and esterified sulfonate to boron-containing radicals is from 0.8:1 to 1.2:1.

7. The process as claimed in claim 6, wherein one or more monomers of the formula IIa:

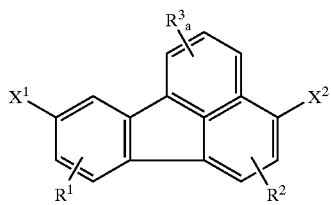

IIa are reacted with one another.

8. The process as claimed in claim 7, wherein $R^1$ to $R^3$ in the formula IIa are each hydrogen.

9. The process as claimed in any of claim 6, wherein Pd is present in the oxidation state 0.

10. A process for preparing a polymer as claimed in claim 1 or 2, which comprises:
photochemically or thermally polymerizing monomers of the formula VI:

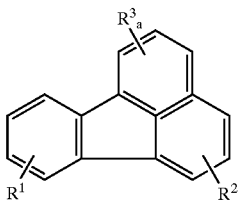

wherein at least 2 of the radicals $R^1$ to $R^3$ are each $Y^1$, and $Y^1$ are identical or different and are selected from the group consisting of —CH=CH$_2$, trans-CH=CH—C$_6$H$_5$, cis-CH=CH—C$_6$H$_5$, acryloyl, methacryloyl, a-methystyryl, para-methylstyryl, —O—CH=CH$_2$, glycidyl,

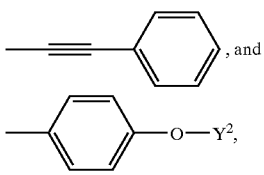

wherein $Y^2$ is selected from among the group consisting of acryloyl, methacryloyl, a-methylstyryl, para-methylstyryl, O—CH=CH$_2$ and glycidyl.

11. The process as claimed in claim 10, wherein monomers of the formula VIa:

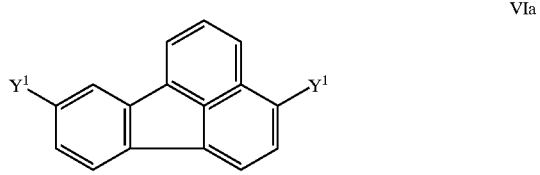

are thermally or photochemically polymerized with one another.

12. A film, comprising: a polymer as claimed in claim 1 or 2.

13. The polymer as claimed in claim 2, comprising: from 1 to 10 repeating units of the formula Ia.

14. The polymer as claimed in claim 2, comprising from 2 to 4 repeating units of the formula Ia.

* * * * *